United States Patent [19]
Terhune et al.

[11] Patent Number: 5,435,186
[45] Date of Patent: Jul. 25, 1995

[54] ULTRASONIC PARAMETRIC AMPLIFIER

[75] Inventors: James H. Terhune, San Jose; Khosrow Karim-Panahi, Palo Alto, both of Calif.

[73] Assignee: General Electric Company, Schenectady, N.Y.

[21] Appl. No.: 966,474

[22] Filed: Oct. 26, 1992

[51] Int. Cl.⁶ .................................... G21C 17/00
[52] U.S. Cl. ................................. 73/642; 73/632
[58] Field of Search .............. 73/642, 632; 330/4.5, 330/4.6, 5.5

[56] References Cited

U.S. PATENT DOCUMENTS

| | | | |
|---|---|---|---|
| 3,233,183 | 2/1966 | Quate | 330/4.6 |
| 3,568,080 | 3/1971 | Troutman | 330/5.5 |
| 3,634,774 | 7/1970 | Carr | 330/4.6 |
| 3,873,858 | 3/1975 | Burke et al. | 330/5.5 |
| 4,025,876 | 5/1977 | Fletcher et al. | 330/5.5 |
| 4,543,533 | 9/1985 | Minigawa et al. | 330/5.5 |
| 4,839,607 | 6/1989 | Schink | 330/4.6 |
| 4,928,069 | 5/1990 | Schink et al. | 330/5.5 |

OTHER PUBLICATIONS

Terhune et al., "Wave Motion of a Compressible Viscous Fluid Contained in a Cylindrical Shell", Proc. ASME PV&P Conf., New Orleans, vol. 231 (1992), pp. 41-50.

Abramowitz et al., Handbook of Mathematical Functions, NBS Applied Mathematics Series 55, U.S. Printing Office, Washington, D.C. (1964), pp. 722, 728-730.

Landau et al., Fluid Mechanics, Addison-Wesley, Reading, Massachusetts (1959), pp. 291-294.

Morse et al., Theoretical Acoustics, Princeton Univ. Press, Princeton, New Jersey, pp. 249, 276-277.

*Primary Examiner*—Richard E. Chilcot, Jr.
*Assistant Examiner*—R. Biegel
*Attorney, Agent, or Firm*—James E. McGinness

[57] ABSTRACT

An ultrasonic parametric amplifier incorporates a duct having rigid cylindrical wall with a periodic inner surface that undulates sinusoidally in an axial direction, and an element for heating the external surface of the wall. The sinusoidal undulations of the periodic inner surface have a wavelength which is about half of the wavelength of the waves of ultrasonic energy propagating through a fluid filling the duct. The waves are amplified by synergistic interactions of the ultrasonic waves with the periodic duct walls when heat is added in a predetermined manner, thereby compensating for the exponential decrease in fluid temperature which would otherwise lead to detuning of the amplifier.

20 Claims, 2 Drawing Sheets

ULTRASONIC PARAMETRIC AMPLIFIER

FIELD OF THE INVENTION

This invention relates generally to non-destructive examination of material, such as metal, for voids, flaws, cracks and other defects that can be detrimental to the integrity of the material. Specifically, the invention relates to the ultrasonic inspection of nuclear and non-nuclear components at operating plants and facilities.

BACKGROUND OF THE INVENTION

Ultrasonic inspections of reactor components usually require substantial amounts of power from the transducers producing the signals. This power is presently achieved by driving the ultrasonic transducer with electronic power amplifiers that are expensive, bulky and unreliable to some degree. In addition, the transducer signal typically has a sizeable bandwidth, which distributes the sonic energy over a considerable range of frequencies.

There are substantial benefits that accrue to narrow-band ultrasonic sources of short duration in time (so-called "tone-burst" signals). This can also be achieved to some degree using electronics components and conventional sources known to the art, but such a process is expensive and less than ideal technically. Rather, some inexpensive, reliable and compact means of generating the ultrasonic energy with narrow bandwidth would simplify the design and operation of many inspection systems.

Analysis of the interaction of a viscous and compressible fluid with an infinitely long, rigid cylindrical shell, whose variable radius fluctuates sinusoidally about a mean value along its axis, has lead to the discovery of a solution to the problem of amplifying ultrasound over long paths inside vessels of nuclear reactors. That analysis is set forth briefly below.

Ultrasonic waves propagating in fluid-filled ducts are essentially compressive in nature, in the sense that the fluid motion is parallel to the direction of propagation. The three-dimensional propagation of sound in fluid-filled ducts has been studied in detail theoretically and is now understood for thin, flexible duct walls and viscous fluids. It is clear that one possible mode of propagation is axisymmetric with negligible damping (at sufficiently high temperature), wherein the radial mode shape is inconsequential. These findings have led to the disclosure of devices useful as ultrasonic waveguides at frequencies of a few megahertz.

As a wave propagates axially in viscous fluid in a rigid cylindrical shell having a wavy wall, internal energy of the fluid is continuously and reversibly exchanged with the intensity of the wave. Ideally there is no net increase of entropy in the process, since heat transfer is neglected between the fluid and the wall of the rigid cylindrical shell. Under ordinary conditions, in which the system parameters take on arbitrary values, the wavy wall of the shell has no unusual effect on the fluid motion, and the damped wave propagation is readily described by the well-known fluid momentum and continuity equations for adiabatic, isentropic flow.

However, there exists a special case for which the wave intensity grows with distance along the duct, due to interaction of the fluid with the periodic wall. This occurs when the wavelength of the wall perturbation is about half that of the fluid wave. The transformed equation describing the wave motion is the Mathieu-Hill equation, whose solutions (Floquet functions) are known to possess regimes of instability for certain ranges of the parameters in the equation. The invention lies in the recognition that a fluid instability, akin to parametric amplification, can result from the interaction of the fluid with the periodic wall of the shell.

From a lengthy analysis, it can be shown that the wave velocity scalar potential $\phi$ is a solution of the Mathieu-Hill equation in the form:

$$\frac{\partial^2 \phi}{\partial y^2} + [\alpha - 2q\cos(\gamma y)]\phi = 0$$

where $q = \epsilon/R << 1$; $R$ is the shell nominal (or mean) radius; $\epsilon$ is the amplitude of the periodic wall perturbation (variation in radius); $\gamma$ is the ratio of the wall perturbation wavelength to the sonic wavelength; $y = (1-q)kz$ is the normalized axial coordinate; $k$ is the ultrasonic wavenumber; $z$ ($>0$) is the axial coordinate; and $\alpha$ is a constant ($\sim 1$).

This deceptively simple equation results when the viscous damping is negligible and the bulk fluid temperature is nearly constant (isothermal fluid for all $z$). In particular, for $\alpha = 1$ and $\gamma = 2$, series solutions are known of the general form:

$$\phi_\nu(y) = e^{i\nu y}P(y); \nu = \nu(\alpha, q)$$

and the solutions display the property:

$$\phi_\nu(y+n\pi) = e^{i\nu(y+n\pi)}P(Y)$$

Thus, there is periodicity of $\pi$ (the Floquet condition), consistent with the nature of the periodic coefficient in the differential equation above. The series representations of the Floquet solutions are known as Mathieu functions.

The characteristic exponent $\nu$ is generally complex and depends on the parameters $\alpha$ and $q$ in a complicated way. Numerical means exist for computing $\nu(\alpha, q)$, including expansions for fixed $\nu$, $q$ when $q << 1$ and $\nu$ is non-integral (the case here); e.g., $$\alpha = \nu^2 + \frac{q^2}{2(\nu^2 - 1)} + \frac{(5\nu^2 + 7)q^4}{32(\nu^2-1)^3(\nu^2-4)} + \ldots ;$$

$$\nu \neq 1, 2, 3 \ldots$$

Neglecting terms of order greater than $q^2$, and taking $\alpha = 1$, the characteristic exponent is a root of $$1 = \nu^2 + \frac{q^2}{2(\nu^2-1)}$$

This quartic equation has two complex roots whose real parts are positive:

$$\nu \approx \sqrt{1 \pm i\frac{q}{\sqrt{2}}} \approx 1 \pm i\frac{q}{2^{3/2}} ; q << 1$$

The solution with positive real part and negative imaginary part represents an exponentially increasing solution as the wave propagates toward $+z$. We say that the solution is unbounded for this particular choice of the parameters; that is, parametric amplification results. On the other hand, the solutions with negative real part and positive imaginary part represent waves traveling toward $-z$ and also growing in amplitude. A typical solution for a growing wave is illustrated in FIG. 1.

Clearly, this amplification only results for exceptional combinations of the parameters in the Mathieu equation. This can be seen from a detailed analysis of the Mathieu functions for arbitrary, but real, parameters ($\alpha$, q). It happens that zones exist in the ($\alpha$, q)-plane in which $\nu$ is real and negative, so stable solutions exist. Other zones exist in which $\nu$ is complex, and at least one unstable solution exists. The first two stable zones are separated by a zone of instability connected at $\alpha = 1$, as shown in FIG. 2.

For $\alpha = 1$ and $q > 0$, which is the case of interest here, the solution lies in the first unstable region. Of course, $\gamma$ can deviate slightly from 2, the effect of which could lead to solutions in the stable zones. A typical solution for a stable wave is illustrated in FIG. 3, in which the wave amplitude is variable, but does not increase with distance. In fact, the wave amplitude displays "beats", because the wavelengths of the wall and the ultrasonic wave are slightly, but not grossly different.

Evidently, sufficiently large deviations from $\gamma = 2$ place $\nu$ in the stable regions above and/or below the first zone of instability; the boundary of the unstable zone is not strictly symmetrical. Conversely, sufficiently small deviations from $\gamma = 2$ do not allow the boundary of the unstable zone to be reached; the perturbed solution remains unstable in this case, depending on the size of q. In particular, a straight-forward thermodynamic argument reveals that for adiabatic walls the wave intensity grows at the expense of fluid internal energy, or temperature. As the wave propagates and grows, the gas is cooled slightly and $\gamma$ decreases, causing the characteristic exponent to eventually move into the first stable zone of FIG. 2. This results in no further amplification, unless the fluid is a good conductor of heat, in which case the temperature gradient is equilibrated and growth may continue.

SUMMARY OF THE INVENTION

The present invention is based on the above-discussed property of fluid-shell interactions when the shell inner surface is periodic and has periodicity specifically and accurately related to that of the sound waves propagating in the fluid contained within the shell. In accordance with the invention, parametric amplification is achieved by synergistic interactions of the sound waves with the periodic duct walls when heat is added in a predetermined manner, thereby compensating for the exponential decrease in fluid temperature which would otherwise lead to detuning of the amplifier.

The invention utilizes the properties of wave propagation in fluids interacting with periodic walls to effectively transport and amplify ultrasonic energy over substantial distances for purposes of increasing the wave intensity without active electronic devices.

The invention employs traveling ultrasonic waves of specific wavelength, frequency and bandwidth interacting with heated, periodic walls having spatial wavelength in specific proportion to the sonic wavelength in order to produce an intense, narrow-band source or detector of pulsed ultrasound.

The invention utilizes the unique properties of fluid-shell interactions in combination with heat transfer properties of fluid-filled shells to provide a means of amplifying ultrasound passively without supplying electronic energy. In particular, it employs a synergistic relationship between the thermomechanical and the ultrasonic properties of the fluid-shell interaction to allow significant parametric amplification to occur in special circumstances that would otherwise deny the possibility of energy exchange from the bulk fluid to the wave.

In accordance with a further aspect of the invention, it is amenable to remote pulse-echo amplification, if the application requires. This can be accomplished using standard transducers of common bandwidth and nominal frequency. The invention amplifies the energy in a direction specified by the wave propagation constant, either in the transmit or receive mode of operation.

Also, use of the invention significantly enhances the sonic intensity at the exit window, even in the presence of viscous and thermal conductivity absorption, in order to efficiently deliver energy to and from the volume being inspected in non-destructive examination applications.

In the presence of periodic inner wall surfaces of cylindrical shape, the waves traveling axially in a viscous fluid must conserve mass in their interactions with the walls. The waves of a specific frequency interact with the walls in a way such that energy is continuously transferred from the bulk fluid to the wave, thereby causing it to grow in intensity, or amplitude. The growth is most appreciable for rigid metallic walls that are heated in accordance with the invention to optimize the fluid-shell interaction.

BRIEF DESCRIPTION OF THE DRAWINGS

These and other advantages of the invention will be better understood when the detailed description of the preferred embodiments of the invention is read in conjunction with the drawings, wherein.

DETAILED DESCRIPTION OF THE PREFERRED EMBODIMENTS

Figure 1:
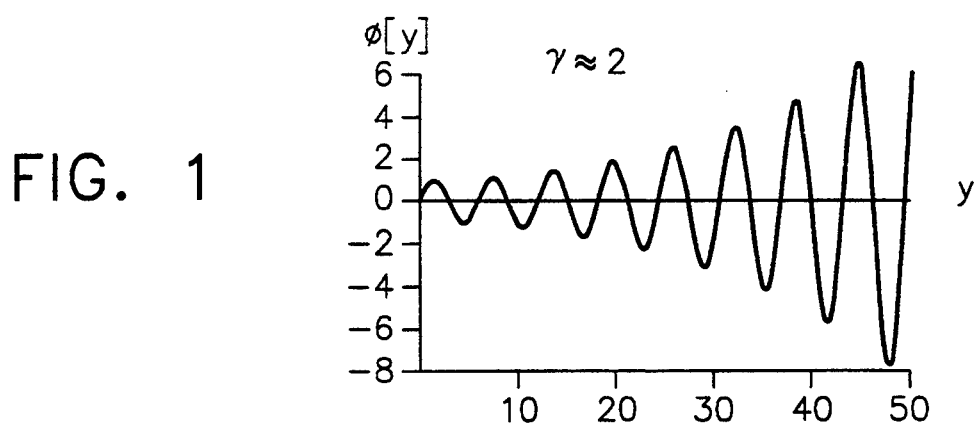
FIG. 1 is a graph depicting the numerical solution of the Mathieu equation for $\alpha = 1$, $q = 0.1$, $\gamma = 2$, $\phi[0] = 0$, $\phi'[0] = 1$.

The ultrasonic parametric amplifier in accordance with a preferred embodiment of the invention, as shown in FIG,, 4, comprises a rigid duct 4 filled with viscous fluid 2. Duct 4 has a periodic wall with an inner surface which is axisymmetric.

The fluid 2 in the metal duct 4 (not shown to scale) is excited at the design frequency by a driving signal imposed on a transducer 6 by external signal generator electronics (not shown). The transducer produces ultrasonic energy which is focused by lens 8. This focused ultrasonic energy excites a metal diaphragm 9 coupled to an exciter pin 10 located at the focus of lens 8. The diaphragm produces an ultrasonic compressional wave with wave number k which enters the waveguide through pin 10 and propagates axially in the fluid,, The traveling wave is a continuous wave, or "burst" which travels along the duct 4 and radiates out a window 12 which closes the opposite end of the duct and is secured to the inner surface of the duct wall by bonding material 14. Reverberations and reflections are controlled by the rubber membrane 11 behind the diaphragm 9, which is an efficient absorber of ultrasonic energy. The energy radiated at the exit window 12 is a burst of essentially plane waves, which can be concentrated by a small lens (not shown) near the output, if required by the application. The window material should be made of a material with acoustic impedance close to that of the fluid (e.g., LUCITE for water).

Figure 2:
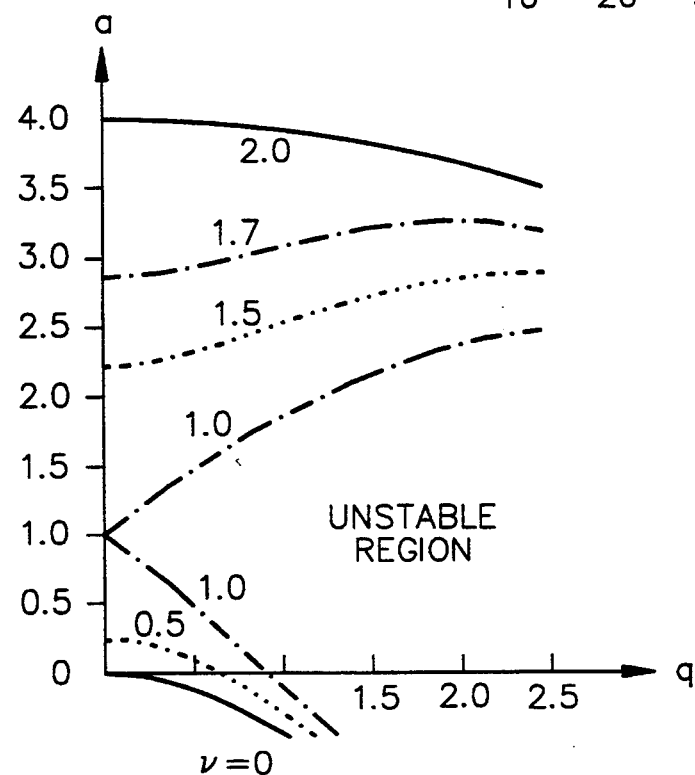
FIG. 2 is a graph depicting the characteristic exponent $\nu$ in the ($\alpha$, q)-plane with stable regions for $0 \leq \nu \leq 1$ and $\leq \nu \leq 2$ respectively.
Figure 3:
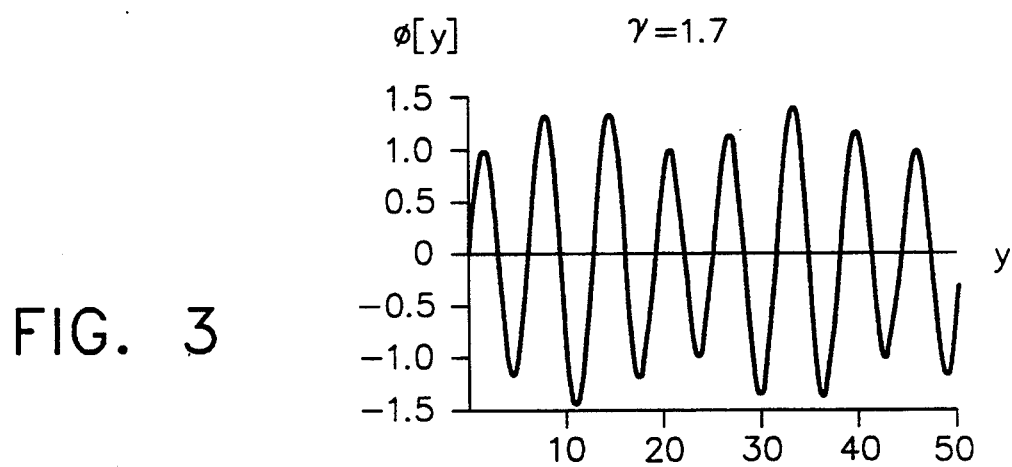
FIG. 3 is a graph depicting the numerical solution of the Mathieu equation for $\alpha = 1$, $q = 0.1$, $\gamma = 1.7$, $\phi[0] = 0$, $\phi'[0] = 1$.
Figure 4:
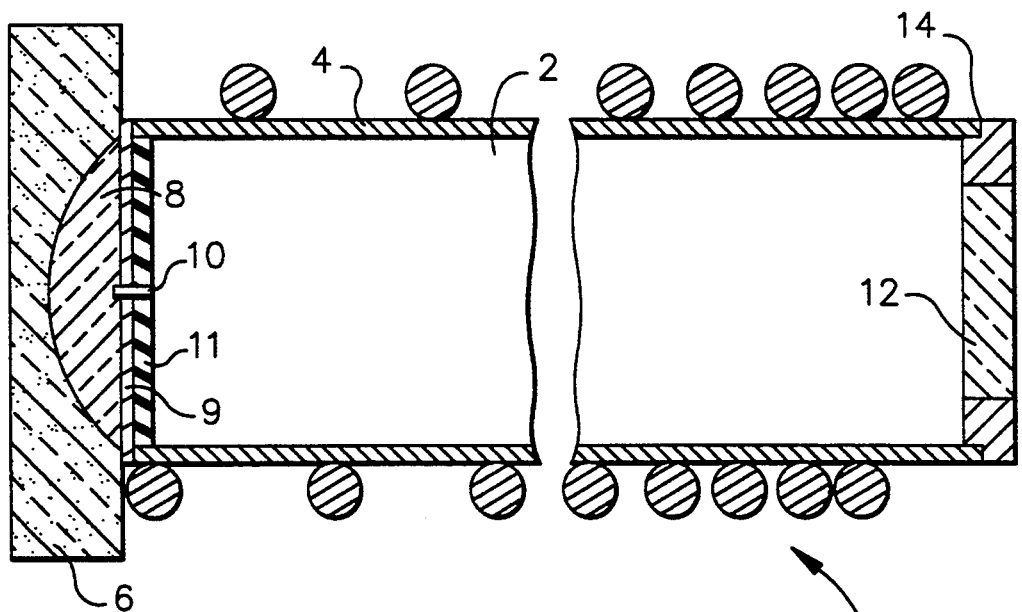
FIG. 4 is a schematic view of an ultrasonic parametric amplifier in accordance with a preferred embodiment of the invention.
Figure 5:
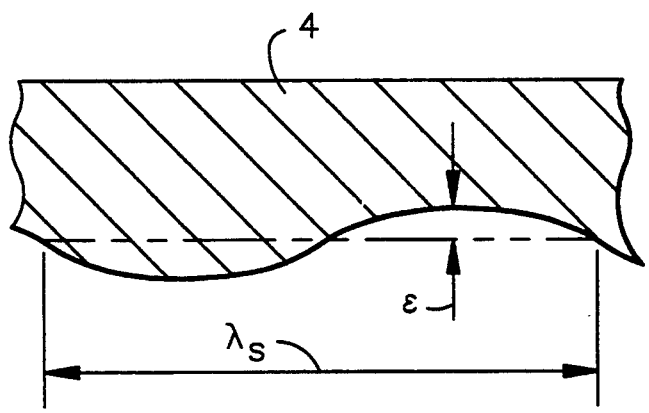
FIG. 5 is a diagram showing a portion of the periodic surface of the duct wall incorporated in the preferred embodiment of the invention.

The duct wall can be either rigid or flexible, but is most useful when made of metal, a preferred material. The duct walls are designed to be relatively rigid, either by thickness or by the stiffening effect of a metal-jacketed variable-pitch heater coil 16. The inner surface of the duct wall is machined to close tolerance with a sinusoidally varying radius. The variation of the radius is small compared to the nominal or rms-value. Referring to FIG. 5, the radius of the inner surface of the periodic wall of duct 4 varies sinusoidally about a mean radius R with a wavelength $\lambda_s = \lambda/2(1-q)$, where $q = \epsilon/R \ll 1$. The machining of surface fluctuations having a wavelength $\lambda_s$ is digitally controlled to the proper value for the frequency of ultrasound to be amplified. This is the means of "tuning" the amplifier, or selecting the sonic wavelength and frequency so that the amplitude will grow as the ultrasonic wave propagates. Actually, a narrow band of frequencies will be amplified, but the bandwidth can be made very small by design. The device is inherently narrow-band (because of the placement of q in the unstable region of FIG. 2 for $\alpha = 1$). Thermal equilibrium is achieved before introducing the ultrasonic wave.

As previously discussed, amplification of the propagating wave results in a decrease in the temperature of fluid 2 which would "detune" the amplifier if left uncompensated. However, if the duct wall is a good heat conductor, such as a metal, then the cooling of the fluid can be offset by heat addition, thereby maintaining nearly isothermal conditions in the wave propagation. Examination of the thermomechanics of this systems leads to an energy balance equation for the fluid:

$$p_0 k^2 \phi(z) = \frac{2h}{R}(T_0 f(z) - T) - \rho_0 c_v c \frac{\partial T}{\partial z}$$

where $P_0$, $\rho_0$, $T_0$ are the bulk fluid pressure, density and absolute temperature, respectively; h is the heat transfer coefficient for the shell wall and the fluid; c is the sonic velocity in the fluid; $c_v$ is the specific heat at constant volume for the fluid; T is the local absolute temperature of the fluid; and f(z) is the wall absolute temperature profile. This equation shows that the fluid remains isothermal in the presence of a growing acoustic wave if for $\delta T/\delta Z = 0$ and $T = T_0$:

$$p_0 k^2 \phi(z) = \frac{2hT_0}{R}(f(z) - 1)$$

Therefore, for liquids or gases at constant axial temperature $T_0$, we require:

$$f(z) = 1 + \frac{p_0 R k^2 \phi_0}{2hT_0} e^{sy} P(y); \quad s = Re[\nu]$$

The periodic function P(y) is not important in practice; only the envelope need by considered. Thus, by defining the spatial average:

$$(\phi_0)_{rms} \equiv \phi_0 \left[ \frac{1}{\pi} \int_0^{\pi} P^2(y) dy \right]^{\frac{1}{2}}$$

the required temperature profile in the wall is $$f(z) = 1 + \frac{p_0 R \omega^2 (\phi)_{rms}}{2c_0^2 h T_0} (e^{s(1-q)kz} - 1)$$

This particular function offsets the adiabatic cooling effect and renders the fluid essentially isothermal, thereby allowing the wave intensity to grow indefinitely as it propagates toward $+z$. The inclusion of viscous heating and thermal conduction effects only lessen the amount of heat addition required, which is quite nominal for tubes with small Z.

The required heat addition is proportional to the fluid density, the duct radius and the frequency squared. The fluid temperature enters the equation via the sonic velocity and the heat transfer coefficient, which are functions of the fluid used. The coefficient $<\phi>_{rms}$ can be computed numerically from the Mathieu functions and is independent of fluid or duct properties. Therefore, the heat addition is essentially exponential with distance in the preferred configuration, although it may be possible to use piecewise linear profiles and/or other heat addition functions. All of these variations are included within the scope of the claimed invention.

In particular, a constant-wall temperature profile (f[z]=1), e.g., using a constant-pitch heating coil, results in fluid temperature given by:

$$\frac{T}{T_0} = 1 - B\frac{(e^{sy} - e^{-\beta y})}{(s + \beta)}$$

Where $\beta$ is the dimensionless ratio Nu/RePr; Nu is the effective Nusselt number; Re is the effective Reynolds number; and Pr is the effective Prandtl number. These numbers are defined by the following:

$$Re = \frac{R^2 \omega}{\nu_0}; \quad Pr = \frac{c_p \mu_0}{K}; \quad Nu = \frac{hD}{K}$$

$$\gamma_0 = \frac{c_p(T_0)}{c_v(T_0)}; \quad D = \frac{2R\gamma_0}{1-q}; \quad B = \frac{p_0 \omega (\phi_0)_{rms}}{\rho_0 c_v T_0 c_0^2 (1-q)}$$

where $c_p$ is the specific heat of the fluid at constant pressure; k is the thermal conductivity of the fluid; $\nu_0$ is the kinematic viscosity of the fluid; $\mu_0$ is the fluid viscosity of the first kind ($=\rho_0 \nu_0$); $c_v$ is the specific heat of the fluid at constant volume; $\omega$ is the radian frequency of the ultrasonic wave; and D is the effective diameter for heat addition.

In the case of $\beta \gg s$, the fluid temperature varies with axial distance like:

$$\frac{T(\beta y > 4)}{T_0} \simeq 1 - \frac{B}{\beta} e^{sy}; \beta >> s$$

Therefore, the fluid temperature variation can be minimized by designing the thermal properties of the system so that $\beta$ is large and B is small. Although suboptimal, this is sufficient in many practical situations.

Similar considerations apply to waveguides of rectangular, elliptical or other cross section. The physical principles are essentially the same as for the cylindrical waveguide, which is a preferred configuration. Furthermore, there are a large number of fluids and ducts that are feasible for use in combination, and those discussed herein do not constitute an exclusive list. These variations are included within the scope of the present invention.

Also, amplification can occur for waves propagating in either direction when the walls are uniformly heated. This is because the characteristic exponent exhibits solutions with negative real part and positive imaginary part, as discussed above. The two-way amplification that results is limited by the need for constant wall temperature, which eventually inhibits intensity growth in both directions of propagation. For one-way propagation, unlimited growth is possible, in principle, using the proper wall temperature profile. Reflections would not grow substantially, in this case, as they would in the case of uniform wall temperature.

Typical values of the various parameters for ultrasound at a frequency of 1.5 MHz in water are: $\lambda=0.987$ mm; $\lambda_s=0.519$ mm; $R=2$ mm; $\epsilon=0.1$ mm; $q=0.05$; $\gamma=2$; $\alpha=1$; $T_0=450°$ K.; $P_0=1$ atm; $<\phi_0>_{rms}1$ mm$^2$/sec; $\nu=1-0.02i$; $y=5.97z$ mm$^{-1}$.

All dimensionless ratios required can be calculated from these quantities and the properties of the fluid (typically water) and the duct material (typically steel). The duct wall is chosen to be thick enough (~2-4 mm) that it is essentially rigid for purposes of wave propagation.

We claim::
1. An ultrasonic amplifier comprising:
   a duct having cylindrical wall means, said wall means having a periodic inner surface which undulates sinusoidally in an axial direction,
   means for heating said wall means, said heating means being coupled to said duct transducing means for transforming electrical energy into waves of ultrasonic energy.
2. The ultrasonic amplifier as defined in claim 1, wherein said wall means is rigid.
3. The ultrasonic amplifier as defined in claim 1, wherein said wall means has an axisymmetric inner surface with a radius that varies sinusoidally about a mean radius in said axial direction.
4. The ultrasonic amplifier as defined in claim 1, wherein said heating means comprises a heating coil helically wound around said wall means.
5. The ultrasonic amplifier as defined in claim 4, wherein said heating coil has a variable pitch.
6. The ultrasonic amplifier as defined in claim 1, wherein the amount of heat added by said heating means to said wall means per unit length of said duct means increases in a first axial direction.
7. The ultrasonic amplifier as defined in claim 6, wherein said increase is exponential.

8. A system for supplying an amplified ultrasonic signal, comprising:
   a duct having cylindrical wall means, said wall means having a periodic inner surface which undulates sinusoidally in an axial direction;
   transducing means for transforming electrical energy into waves of ultrasonic energy having a first predetermined wavelength and a first predetermined amplitude, said transducing means being situated at one end of said duct;
   a fluid medium filling the space inside said duct; and
   means for heating said wall means, said heating means being coupled to said duct,
   wherein said sinusoidal undulations of said periodic inner surface have a second predetermined wavelength, the ratio of said first predetermined wavelength to said second predetermined wavelength being approximately equal to 2, the interaction of said fluid with said sinusoidal undulations producing waves of ultrasonic energy having said first predetermined wavelength and a second predetermined amplitude, said second predetermined amplitude being greater than said first predetermined amplitude.
9. The system as defined in claim 8, wherein said wall means is rigid.
10. The system as defined in claim 9, wherein said wall means has an axisymmetric inner surface with a radius that varies sinusoidally about a mean radius in said axial direction, the ratio of said first predetermined wavelength to said second predetermined wavelength being equal to $2(1-q)$, where q equals the maximum height of the variation from said mean radius divided by said mean radius.
11. The system as defined in claim 8, wherein said heating means comprises a heating coil helically wound around said wall means.
12. The system as defined in claim 11, wherein said heating coil has a variable pitch.
13. The system as defined in claim 8, wherein the amount of heat added by said heating means to said wall means per unit length of said duct means increases in a first axial direction.
14. The system as defined in claim 13, wherein said increase is exponential.
15. The system as defined in claim 8, further comprising exit window means for allowing transmission of ultrasonic energy therethrough, said exit window means being situated at the other end of said duct means, said exit window means, transducing means and duct means forming a fluid-tight volume filled by said fluid medium.
16. A method for supplying an amplified ultrasonic signal comprising the steps of:
   filling a duct having cylindrical wall means with a fluid medium, said wall means having a periodic inner surface which undulates sinusoidally in an axial direction;
   transmitting waves of ultrasonic energy having a first predetermined wavelength and a first predetermined amplitude into said duct means in said axial direction; and
   heating an external surface of said wall means while said waves of ultrasonic energy having said first predetermined wavelength are propagating through said duct means in said axial direction,
   wherein said sinusoidal undulations of said periodic inner surface have a second predetermined wavelength, the ratio of said first predetermined wavelength to said second predetermined wavelength being approximately equal to 2, the interaction of said fluid with said sinusoidal undulations producing waves of ultrasonic energy having said first predetermined wavelength and a second predetermined amplitude, said second predetermined amplitude being greater than said first predetermined amplitude.

17. The method as defined in claim 16, wherein said wall means has an axisymmetric inner surface with a radius that varies sinusoidally about a mean radius in said axial direction, the ratio of said first predetermined wavelength to said second predetermined wavelength being equal to $2(1-q)$, where q equals the maximum height of the variation from said mean radius divided by said mean radius.

18. The method as defined in claim 16, wherein said heating step comprises supplying electrical energy to a heating coil helically wound around said wall means.

19. The method as defined in claim 16, wherein the amount of heat added by said heating step to said wall means per unit length of said duct means increases in a first axial direction.

20. The method as defined in claim 19, wherein said increase is exponential.

* * * * *